(12) United States Patent
Ocelic

(10) Patent No.: US 9,043,946 B2
(45) Date of Patent: May 26, 2015

(54) METHOD FOR MEASURING THE NEAR-FIELD SIGNAL

(71) Applicant: Neaspec GmbH, Martinsried (DE)

(72) Inventor: Nenad Ocelic, Martinsried (DE)

(73) Assignee: Neaspec GmbH, Martinsried (DE)

( * ) Notice: Subject to any disclaimer, the term of this patent is extended or adjusted under 35 U.S.C. 154(b) by 0 days.

(21) Appl. No.: 14/349,801

(22) PCT Filed: Dec. 19, 2012

(86) PCT No.: PCT/EP2012/076068
§ 371 (c)(1),
(2) Date: Apr. 4, 2014

(87) PCT Pub. No.: WO2013/102561
PCT Pub. Date: Jul. 11, 2013

(65) Prior Publication Data
US 2015/0089694 A1    Mar. 26, 2015

(30) Foreign Application Priority Data
Jan. 5, 2012  (EP) .................................... 12150325

(51) Int. Cl.
*G01Q 60/18*    (2010.01)
*H04B 5/00*     (2006.01)
*G01N 21/47*    (2006.01)

(52) U.S. Cl.
CPC .............. *G01Q 60/18* (2013.01); *H04B 5/0031* (2013.01); *H04B 5/0043* (2013.01); *G01N 21/47* (2013.01); *G01N 2201/101* (2013.01)

(58) Field of Classification Search
USPC .............. 850/1, 2, 3, 5, 21, 22, 24, 30, 31, 32
See application file for complete search history.

(56) References Cited

U.S. PATENT DOCUMENTS 8,793,811 B1 * 7/2014 Prater et al. ...................... 850/9
2002/0126732 A1 * 9/2002 Shakouri et al. ............... 374/130
2007/0252988 A1 * 11/2007 Levy ............................. 356/328

FOREIGN PATENT DOCUMENTS

DE    100 35 134 A1    2/2002
EP      0 394 668      6/1994
EP    1 205 939 A2    5/2002
EP    1 770 714 A1    4/2007

* cited by examiner

*Primary Examiner* — Nicole Ippolito
(74) *Attorney, Agent, or Firm* — Chalin A. Smith; Smith Patent

(57) ABSTRACT

The present invention relates to a method for measuring the near-field signal of a sample in a scattering type near-field microscope and to a device for conducting said method.

18 Claims, 4 Drawing Sheets

METHOD FOR MEASURING THE NEAR-FIELD SIGNAL

PRIORITY

This application corresponds to the national phase of International Application No. PCT/EP2012/076068, filed Dec. 19, 2012, which, in turn, claims priority to European Patent Application No. 12.150325.4 filed Jan. 5, 2012, both of which are incorporated by reference herein in their entirety.

FIELD OF THE INVENTION

The present invention relates to a method for measuring the near-field signal of a sample in a scattering type near-field microscope comprising a scanning probe and a sample, and to a device for conducting the said method.

BACKGROUND OF THE INVENTION

Optical near-field microscopy is based upon the measurement of scattered light at a near-field probe which is generated by optical near-field interaction between the near-field probe and a sample. To achieve high local resolution known (near-field) probes comprising sharp tips are used, e.g. such probes as used in atomic force microscopy. The (near-field) probe is illuminated at its tip by focused light, e.g. in the visible or mid-infrared spectrum, to generate scattered light during tip-specimen interaction. The optical near-field of the sample is typically determined by scanning (scan-probing) the sample with the probe. From the measurement of the light scattered by the probe, in particular the near-field signal, material properties of the sample can be obtained with a local resolution down to nanometer scale without limitations imposed by diffraction of light.

An apertureless near-field optical microscope is disclosed in EP 394 668 B1.

The light scattered by the tip of the probe (in the following only "probe") is collected since it conveys the information on the local optical properties of the sample. The presence of a sample (also referred to as specimen) in close proximity to the tip modifies the scattered light amplitude and phase because the scattering depends not only on the tip alone, but on the polarizability of the entire coupled probe-sample system. The optical resolution of the near-field microscope is essentially limited only by the tip radius.

The general problem of scattering type near-field optical microscopes is that the largest part of the collected light does not originate from the tip apex. Instead, it is mostly produced by reflections and scatterings from the tip shaft and the entire illuminated area of the sample. This undesirable part of the signal is commonly referred to in the art as background signal, or background light. Several methods to avoid the background signal are known in the art.

EP 1 770 714 A1 discloses a method for reducing the background signal by demodulating the scattered light at the frequency of the higher harmonics of the tip oscillation. This way, the near-field signal to background signal ratio can be significantly improved, as indicated in FIG. 1. While the unmodulated background signal (B0) is significantly larger than the unmodulated near-field signal (N0), the near-field signal at the first demodulation order (N1) and the background signal at the first demodulation order (B1) are approximately of the same order of magnitude. At the second demodulation order the near-field signal (N2) becomes significantly larger than the background signal (B2). However, as indicated in FIG. 1, by using the second demodulation in order to suppress background signal, the useful signals N0 and N1 are lost, which is of disadvantage as N0 is typically 10 to 100 times higher than N2, and N1 is typically 3 to 10 times higher than N2. Higher demodulation orders lead to even higher loss of near-field signal.

A further method for reducing background interference is disclosed in DE 10 035 134. The disclosed method is based on the detection of the scattering at higher harmonics of the tip oscillation frequency, heterodyned with the reference wave shifted by a specific frequency in respect to the light used for tip and sample illumination. This heterodyne method has the disadvantage that the frequency shift required for heterodyning is produced by an acousto-optical modulator (AOM) which separates the shifted beam only by a small angle from the unshifted beam at its output. The small shift of the modulated beam provides difficulties in the alignment of the light paths. Furthermore, AOMs are expensive and commercially available only for a few wavelength ranges which strictly limits their near-field microscopic, and especially near-field spectroscopic applications.

Therefore, there is still a need in the art for an improved method for measuring the near-field signal of a sample in a scattering type near field microscope which does not show the above mentioned problems of the prior art.

SUMMARY OF THE INVENTION

It has been found that the background signal B of a probe during near-field measurement in a scattering type near-field microscope behaves according to the followed equation (I):

$$B = k^*(e^{i\Delta\phi} + c^* e^{-i\Delta\phi}) + k_0 \qquad (I),$$

wherein $k_0$, k and c are complex constants, and $$\Delta\phi = 2^*\pi/\lambda^* \cos\theta^* H,$$

wherein lambda ($\lambda$) is the wavelength of the light illuminating the tip, $\theta$ is the mean angle of light incidence onto the tip of the probe relative to the tip oscillation, and H is the distance of the probe to the sample. $k_0$ is an offset originating from distance-independent optical and electronic signals.

The values of the constants $k_0$, k and c are not predictable from theory and can vary from one position of the sample in an image (pixel) to another position (pixel). Therefore, for each pixel or output value the constants preferably have to be determined separately.

Generally, the near field signal and the background signal are additive, i.e. addition of both signals leads to the total scattering signal which can be measured. Thus, parameters $k_0$, k and c can be determined when the probe is sufficiently distant from the sample so that the near-field interaction only contributes a negligible value to the total scattering signal. It has been found that a typical distance when the total scattering signal substantially consist of background signal and no significant near-field signal, is for a typical scattering type near-field microscope at a probe to sample distance of about 100-150 nanometers or larger, depending on the sample and the tip radius.

In order to determine the near-field signal, according to the present application the probe to sample distance is increased to a sufficiently large distance where the total scattering signal substantially consists of background signal and no significant near-field signal. When the probe oscillates, the amplitude of the oscillation is increased or the mean distance of the probe to the sample is increased to assure that the probe at least at one position of the oscillation reaches a probe-sample distance where the total scattering signal substantially consists of background signal and no significant near-field signal. According to the above equation (I), the background signal is dependent on the sample to probe distance H. Thus, changing the distance of the probe to the sample leads to a correspondingly changed background signal. This background signal can be correlated to the probe-sample distance and the parameters $k_0$, k and c can be determined by fitting the background function B, which is dependent on the tip-sample distance H as indicated above, to the measured total scattering signal, which substantially comprises background signal.

The equation for the background signal B as indicated above is a non-linear model function, which requires an iterative parameter determination procedure in order to fit the function to the determined scattering signal, which is dependent on the distance. While generally such non-linear functions can be used for real-time (online) processing, fitting said function requires a significant amount of computational power and time. Further, it cannot be guaranteed that the fitting converges to a global optimum for all parameters. Therefore simplification of this function would be desirable in order to simplify real-time processing, in particular to use fit functions with linear dependence on parameters, as these can be fitted by fast, standard linear fitting algorithms known in the art, such as the linear least squares fitting.

It has been found that in order to provide a good measurement of the near-field signal, the background signal B can be determined sufficiently precise, when the background signal is fitted according to at least a first degree approximation in the distance range $H_0$ to $H_1$, where the total scattering signal substantially consist of background signal. The near-field signal at a distance $H_N$ can be calculated by subtracting from the scattering signal, obtained from the probe in proximity to the sample, the background signal extrapolated for distance $H_N$ using said fit coefficients.

The present invention therefore relates to a method for measuring the near field signal of a sample in a scattering type near field microscope comprising a probe and a sample, which method comprises the steps of a) measuring the scattering signal S of the probe as a function of a distance-determining parameter P, whereby the functional dependence H(P) of the probe-sample distance H on P is known, by measuring the scattering signal S(P) for at least two values of the distance-determining parameter P corresponding to two probe-sample distances H in the range $H_0$ to $H_1$, wherein $H_1$ is larger than $H_0$, and the scattering signal S substantially consists of background signal for all distances $H > H_0$, b) determining the fit coefficients of a background fit function B(P), wherein the background fit function is equation (I)

$$B(P) = c0 + c1 * (\exp(i*k*H(P)) + c2 * \exp(-i*k*H(P)))^2 \quad \text{(I)},$$

wherein B(P) is the scattering signal S(P) as measured in step a), c0, c1 and c2 are fit coefficients, k is a fixed parameter or a fit coefficient, or wherein the background fit function B(P) is an at least first order approximation of equation (I) in terms of P, c) measuring the scattering signal $S_N$ of the probe for at least one value of the distance-determining parameter $P_N$ corresponding to a probe-sample distance $H_N$ smaller than $H_0$, and d) determining the near field signal N for at least one value of the distance-determining parameter $P_N$ by subtracting from the scattering signal $S_N$ measured at step c) the background signal $B_N$ which is calculated by extrapolating the background fit function B(P) to the probe-sample distance $H_N$ using the fit coefficients determined in step b).

DETAILED DESCRIPTION OF THE PREFERRED EMBODIMENTS

Figure 1:
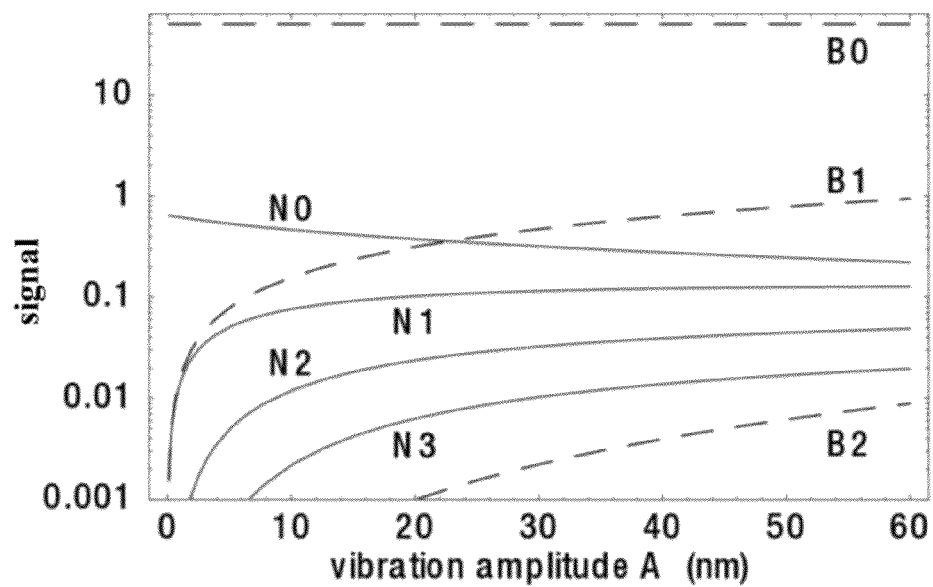
FIG. 1 is a diagram illustrating background signal intensities B0, B1, B2 in relation to near-field signals N0, N1, N2 and N3. The numbers correspond to the demodulation order.

In step a) of the method of the present application the scattering signal S of the probe is measured as a function of a distance-determining parameter P. The distance-determining parameter P is a parameter, from which the probe-sample distance can be determined, i.e. the functional dependence H(P) of the probe-sample distance H on P is known. The scattering signal S(P) is measured for at least two values of the distance-determining parameter P, i.e. corresponding to two different probe-sample distances. The measured scattering signal S is recorded in dependence of the distance-determining parameter P. In step a), the probe-sample distances have to be chosen high enough to assure that the obtained scattering signal S of the probe substantially consists of background signal. Thus, in step a) the scattering signal S is measured for at least two distances H in the range $H_0$ to $H_1$, wherein $H_1$ is larger than $H_0$, and the scattering signal S substantially consists of background signals for all distances $H < H_0$.

In step a), for measuring the scattering signal, the probe to sample distance has to be set to the distance $H_0$, which comprises positioning the probe in a distance $H_0$ to the sample, or positioning the sample relative to the probe to achieve a probe-sample distance $H_0$, dependent on the system used. Thus, if a system is used, wherein the probe is moved, while the sample is fixed, the probe is positioned in the distance $H_0$, whereas if the sample is moveable, and the probe is fixed or is only oscillating, the sample is moved in order to set the (mean) probe-sample distance to $H_0$. The scattering signal S is measured in step a) for at least 2 values, preferably at least 3 values, in particular at least 5 values, e.g. at least 10 values or at least 20 values of the distance-determining parameter P (corresponding to the respective numbers of probe-sample distances H).

In one preferred embodiment, the value of the distance-determining parameter P corresponds to the probe-sample distance H, i.e. parameter P is linearly dependent on probe-sample distance H. In another preferred embodiment, distance-determining parameter P depends on the voltage applied to an actuator regulating the probe-sample distance, i.e. a linearly dependency between distance-determining parameter P and distance H exists, optionally taking a hysteresis of the actuator into account. Typically an actuator is a piezo-device used e.g. for moving the probe and/or the sample in the device for measuring the near-field. In a further preferred embodiment, the distance-determining parameter P corresponds to the vertical position Z of the sample or the probe as obtainable from a Z-position sensor. The vertical position Z is the direction substantially normal to the sample surface in the direction of the probe. A typical Z-position sensor is e.g. a capacitive position sensor as known in the art, whose capacitance changes in inverse proportion to the distance between the sample and a reference surface. In a further preferred embodiment, the distance dependent parameter corresponds to time T, if the probe-sample distance H predictably depends on time, e.g. in case of an probe oscillating perpendicular to the sample.

Figure 3:
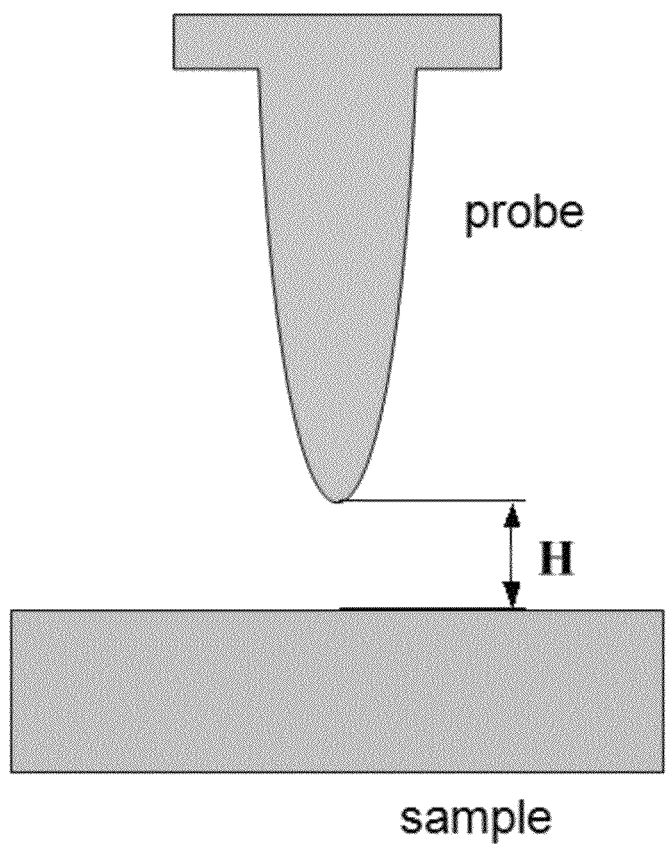
FIG. 3 is a side diagrammatic view of the probe and the sample illustrating the determination of distance H.

In step a) of the method of the present invention the probe is preferably positioned in a distance $H_0$ to the sample as indicated in FIG. 3 and the scattering signal S is measured in dependence of the distance determining parameter P. The distance H is the distance of the sample to the very end of the probe, i.e. the tip. The distance $H_0$ should be chosen such that the scattering signal as obtained from the probe substantially consists of background signal, and no significant near-field signal. In particular, the background signal at $H_0$ should be at least about 90%, more preferably at least about 95%, in particular at least about 98% of the total scattering signal. The distance $H_0$ should preferably be at least 50 nanometers, more preferably at least 100 nanometers, in particular at least 150 nanometers.

Further in step a) of the method of the present invention, the distance H of the probe to the sample is changed, preferably increased, in a range from $H_0$ to $H_1$, and the scattering signal S is measured at at least two distances H. In the range $H_0$ to $H_1$, preferably at least 2 values, more preferably at least 3 values, in particular at least 5, e.g. at least 10, values for the scattering signal S are measured as a function of the distance determining parameter P. Preferably both amplitude and phase of the scattering signal S are measured. In step a) of the method of the present invention, the distance $H_1$ should be at least 10 nanometers, preferably at least 20 nanometers, in particular at least 50 nanometers larger than $H_0$.

In step b) of the method of the present invention, the data of the scattering signal S(P) obtained in step a) is approximated by a function according to equation (I). This means the data of scattering signal S(P), which is dependent on the distance determining parameter P, as obtained in step a) is subjected to function approximation, also known in the art as "curve fitting". I.e. a function according to equation (I) is fitted to the data obtained in step a). The background fit function B(P) corresponds to equation (I), or is an at least first order approximation of equation (I) in terms of P. Typically, the order of the approximation defines the number of fit coefficients. Preferably, the fit coefficients are determined by conducting a first degree, more preferably a second degree, or a third degree, or higher degree approximation for the scattering signal S(P) corresponding to the range $H_0$ to $H_1$ as measured in step a). A first degree approximation according to equation (I) has the advantage of very low demand for computational time for fitting, as only two fit coefficients have to be determined for each set of data. The higher the degree of approximation, the more computational time is necessary, however, the more correct is the approximation. Thus, if a more precise absolute determination of the near-field signal is desirable, a higher degree of approximation should be chosen. A very precise approximation of the scattering signal will be obtained if fit equation (I) as shown above is used. However, this non-linear function requires a significant amount of computational time in order to obtain acceptable fitting of the parameters. In order to reduce computational time, any second or higher order approximation of the equation (I) could be applied. Suitable methods to determine second or higher order approximations from the equation (I) are known in the art, such as e.g. Taylor series expansion in case of linear or polynomial dependence of H on P, or e.g. Fourier series expansion in case of periodic dependence of H on P.

In step c) of the method of the present invention, the scattering signal $S_N$ of the probe is measured for at least one value of the distance-determining parameter $P_N$ corresponding to a probe-sample distance $H_N$ smaller than $H_0$. This means the distance of the probe to the sample is reduced to a distance $H_N$, and the scattering signal $S(P_N)$ of the probe is measured. Typically the distance $H_N$ is lower than 20 nanometers, preferably lower than 10 nanometers, in particular lower than 5 nanometers, or below. This means that the tip is in close proximity to the sample when measuring the scattering signal $S_N$ in order to increase the near-field signal as much as possible.

In step d) of the method of the present invention, the near-field signal N is determined for at least one value of the distance-determining parameter $P_N$ by subtracting from the scattering signal $S_N$ of the probe the background signal $B_N$. The scattering signal $S_N$ is measured in step c) by the near-field microscope at the probe-sample distance $H_N$ corresponding to $P_N$. The background signal $B_N$ is calculated by extrapolating the background fit function B(P) to the probe-sample distance $H_N$ using the fit coefficients determined in step b). E.g. when background fit function B(P) according to equation (I) was used and fit coefficients c0, c1, c2, and optionally k were determined in step b), $B_N$ is calculated by using the corresponding values for fit coefficients and using $H(P_N)$ by inserting the corresponding values into equation (I). Alternatively, if a first, second or higher degree approximation was conducted in step b) and two, three or more fit coefficients were determined, the background signal $B_N$ is calculated by using these two, three or more fit coefficients and the corresponding approximation.

Depending on the sample to be investigated it might be desirable to measure both amplitude and phase of the scattering signal, preferably by means of an interferometric light detection technique as known in the art, and to calculate both the amplitude and phase of the near-field signal accordingly. Therefore, when fitting the scattering signal B(P) in step b), complex fit coefficients have to be used, which is preferred according to the present invention.

In step b) of the method of the present invention, preferably the background fit function B(P) is an at least first order approximation of equation (I) in terms of P. The determination of suitable approximations of background fit function B(P) of at least first order, second order or higher order expansions of equation (I) are known in the art. Preferably approximations are used which are linear in the fit coefficients. Suitable approximations are e.g. Taylor series, Padé approximant, Chebyshev polynomials or generalized Fourier series. If an at least first order approximation of equation (I) is used in step b) of the method of the present invention, a corresponding number of fit coefficients has to be determined depending on the order of the approximation, typically such that the number of fit coefficients is larger by 1 than the order of the approximation.

Preferably, the background fit function B(P) is equation (II)

$$B(P)=c0+(c1*H(P)) \tag{II}$$

wherein B(P) is the scattering signal S(P) as measured in step a), and c0 and c1 are fit coefficients.

In a further preferred embodiment, the background fit function B(P) is equation (III)

$$B(P)=c0+(c1*H(P))+(c2*(H(P))^2) \tag{III}$$

wherein B(P) is the scattering signal S(P) as measured in step a), and c0, c1 and c2 are fit coefficients.

Parameter k in equation (I) in step a) can be a fixed parameter, or a fit parameter, i.e. it can be predetermined as a specific constant, e.g. a constant determined for a specific microscope sample/wavelength system. Alternatively, it can be a fit parameter and is thus determined with the fit coefficients during approximation of the scattering signal according to equation (I).

In a preferred embodiment, the background fit function B(P) is equation (I) and parameter k is a fixed parameter and has a value determined according to the equation (IV)

$$k = 2*\pi/\lambda*\cos(\theta) \quad (IV),$$

wherein $\lambda$ is the wavelength of the light illuminating the probe, and $\theta$ is the mean angle of light incidence onto the tip of the probe relative to the probe oscillation. In this embodiment and preferably for all embodiments of the present invention the probe is oscillating substantially perpendicular to the sample surface.

The scattering-type near-field microscope, also known as apertureless near-field microscope used in the method according to the present invention is generally a device as known in the art comprising a probe, which can brought close proximity to a sample or the sample can be in proximity of the probe, respectively. Preferably, the near-field is measured by scanning (scan-probing) the sample with the probe while measuring the near-field interaction between the probe and the sample by detecting the light scattered from the tip of the scanning probe. Thereby, the scanning motion can be performed by moving the scanning probe over a stationary sample, in which case the focus of the light illuminating the probing tip needs to be large enough to cover the entire range of motion of the tip, or the focus is moved following the tip. In a preferred alternative embodiment the scanning is performed by moving the sample while the probe is stationary. In this embodiment the size of the focal point of the light illuminating the tip is independent of the scan range, and moving the focal point synchronously with the probe can be avoided.

Probes to be used in the scattering type near-field microscope are such comprising a cantilever and a tip, which are known in the art for AFM or for scanning near-field optical microscopy (SNOM). These probes typically comprise a cantilever which carries a tip on one of its ends; the other end of the cantilever is typically mounted onto a larger base to simplify mounting and replacement of the tip. The radius of curvature of the tip of the probe is typically below about 100 nanometers, preferably below about 50 nanometers, most preferably below about 20 nanometers. The tips of the cantilevers may be metalized. These probes comprising suitable tips are commercially available, e.g. from NANOSENSORS™ or MikroMasch™.

In the method described herein consisting of measuring and fitting the background signal at distances $H_0$ to $H_1$, extrapolating the background signal to the distance $H_N < H_0$ and subtracting it from the scattering signal S measured at $H_N$, the scattering signal S, background signal B and near-field signal N are represented as functions of the distance-defining parameter P. As the distance H can be determined when knowing P, the functions S(H), B(H) and N(H) can easily be transformed into a function of P by replacing the parameter H by H(P), wherein H(P) is the mathematical expression for H in terms of P.

In a preferred embodiment of the present invention, in the method of the invention a near-field scan of the near-field signal of the sample is obtained by scanning the probe over the sample, i.e. rastering the sample, and determining the near-field signal for several position of the sample. Typically the probe is scanning the sample in a line by line pattern (or the sample is moved, respectively) to obtain a scan of the sample in two dimensions. Preferably the topography of the sample is measured simultaneously. Preferably for each position (pixel) of the scan, the near-field signals are determined. In such a method, in one embodiment steps a) and b) are conducted only once, e.g. before scanning the sample, once during the scan, or once after the scan. The fit coefficients determined once in step b) are used in this embodiment to determine the near-field signal in step d) for each position (pixel) of the scan of the sample. In a preferred embodiment of the invention, steps a) and b) are conducted for each position (pixel) of the near-field scan. I.e. at each position (pixel) of the scan, the distance H of the probe to the sample is increased to $H_0$, the scattering signal is measured in the range $H_0$ to $H_1$, and the fit coefficients are determined according to steps a) and b) of the method of the invention. Then the near-field signal $S(H_s)$ is determined for this distance $H_s$ according to steps c) and d) of the method of the invention. Generally the order of carrying out step c) with respect to either of the steps a) or b) is arbitrary.

In a particular preferred embodiment of the invention, an oscillation movement of the probe substantially perpendicular to the sample is used during measuring the near-field signal. In this embodiment a sufficiently large oscillation amplitude of the probe can be used such that the oscillation covers the range $H_0$ to $H_1$. This oscillation movement of the probe can be used to measure the scattering signal of the probe as a function of the distance determining parameter P for the range $H_0$ to $H_1$. In order to conduct step a) during said oscillation, an oscillation of the probes substantially perpendicular to the sample is applied, and the amplitude of the oscillation is at least as high as the distance of $H_0$ to $H_1$. Most preferred, the oscillation amplitude is selected such that the tip is in direct contact with sample surface at one endpoint of the oscillation and the oscillation amplitude is at least as large that during the oscillation cycle the distance H of the probe covers the range $H_0$ to $H_1$. In such an embodiment the oscillation movement of the probe can be used for both distance regulation of the probe to the sample and for steps a) and b) of the method of the present invention. Thus, in this embodiment, one complete oscillation cycle or an average oscillation cycle corresponding to the sum or a mean value of a number of oscillation cycles (preferably at least 10, e.g. at least 100 cycles) is preferably used for both determining the scattering signal in relation to the distance in the range of $H_0$ to $H_1$ (step a), as well as for measuring the scattering signal of the probe in proximity to the sample (step c) and optionally step d)). The latter embodiment has the advantage that the fit coefficients to calculate the background signal are determined for each position (pixel) of the near-field scan of the sample and the coefficients and/or the signals may be averaged during scanning the same pixel for increasing signal to noise ratio.

Figure 2:
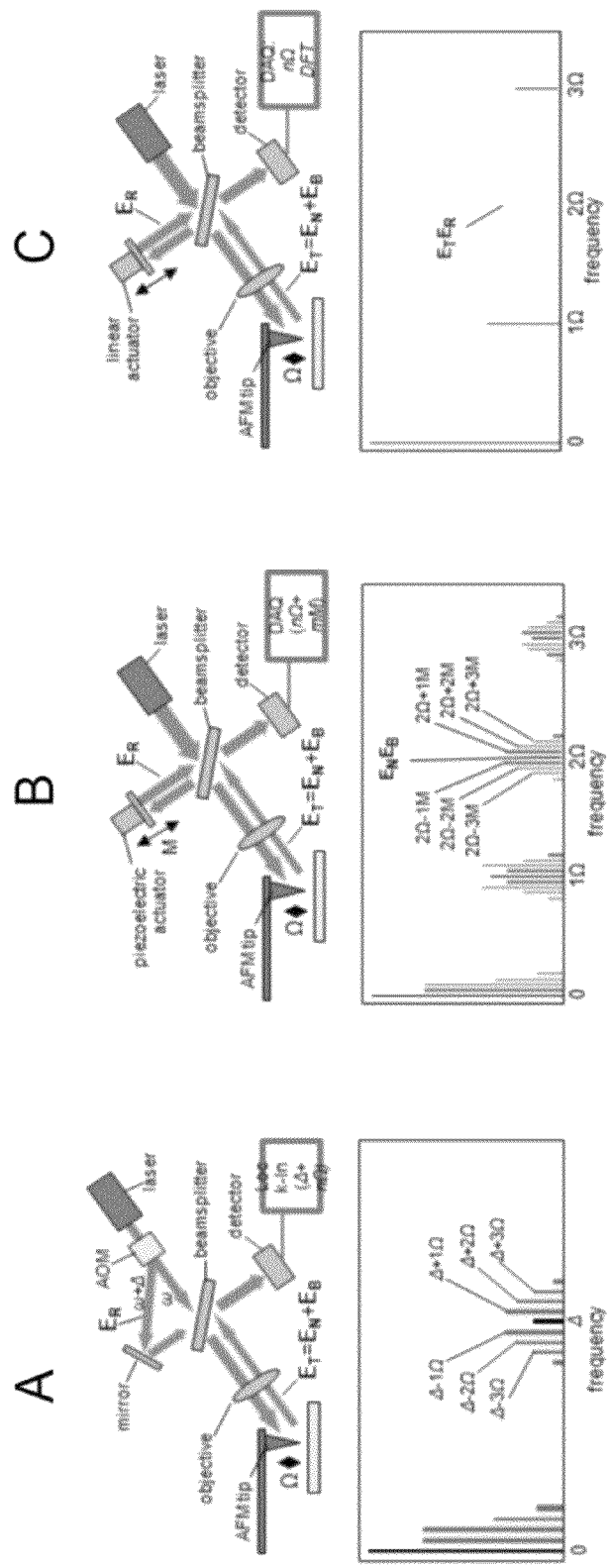
FIG. 2 is a schematic view of heterodyne (A), pseudo-heterodyne (B) and Fourier-transform (C) interferometric detection methods.

The present invention further relates to a device for measuring the near-field signal of a sample suitable for conducting the method as disclosed above. Such device could be based on known near-field optical microscopes, which are combined with suitable devices for data acquisition and computation. Latter devices should be suitable for data acquisition in order to compute both scattering signals as well as distance signals, to determine fit coefficients and for computation of the near-field signal according to steps a) to d) as disclosed above. Suitable devices for acquisition and computation of data are known in the art. For example, known near-field optical microscopes could be equipped with suitable data acquisition devices known in the art, e.g. connected to a suitable personal computer comprising an analog digital converter, wherein the computer is equipped with a software in order to conduct the steps a) to d) of the method of the invention as disclosed above. The near-field optical microscope is preferably equipped with an interferometric detection unit to detect the scattering signal, e.g. it can be equipped with a heterodyne, pseudo-heterodyne or furrier-transform detection method as indicated in FIG. 2. In the device the scattering signal is preferably measured by an interferometric detection method. Preferably at least 3 different interferometer states are used to determine the amplitude and the phase of the scattered light, as described in detail in EP 1 770 714, which is incorporated herein by reference.

The invention is further illustrated by the detailed description of the figures.

In FIG. 1, the results of a theoretical calculation of the near-field (Nn) and background signals (Bn) for a 25-nm broad metalized tip on a silicon sample is shown. The wavelength of the illuminating light was λ=10 micrometer. Index n indicates the harmonic number, i.e. the demodulation order. This figure illustrates that the higher the demodulation order, the more useful near-field signal is lost. E.g. a demodulation order n=3, as suggested in the art to suppress background signals, means signals N0, N1 and N2 are lost.

In FIG. 2, setups for reducing background signal and measuring near-field signal as known in the art are indicated. In the indicated setups, the total scattered electric field $E_T$ consists of the near-field contribution $E_N$ and the background contribution $E_B$ and is brought to interference with a reference electric field $E_R$ at the detector.

Setup A of FIG. 2 indicates a heterodyne setup, i.e. an acousto-optical modulator (AOM) is used for modulating the input laser. AOMs have the disadvantage of rather limited spectral range. Setup A has the advantages of lack of moving parts, simple demodulation and fast measurement. However, it has the disadvantages of the necessity of alignment for each change of wavelength of illuminating light, and of difficult alignment depending on the AOM used.

In setup B of FIG. 2, a pseudo-heterodyne interferometric detection is shown. A piezoelectric actuator moves mirror M in order to modulate the used laser light. This setup has the advantage of unlimited spectral range and less realignment than setup A. However, it has the disadvantage of a moving mirror and complicated demodulation.

Setup C of FIG. 2 shows a Fourier transform setup of an interferometric detection method. Mirror M is linearly actuated. The advantages of the Fourier transform setup are unlimited spectral range and no realignment for a change of the used illumination light. However, the setup has a disadvantage of a moving mirror and a longer measurement time.

Figure 4:
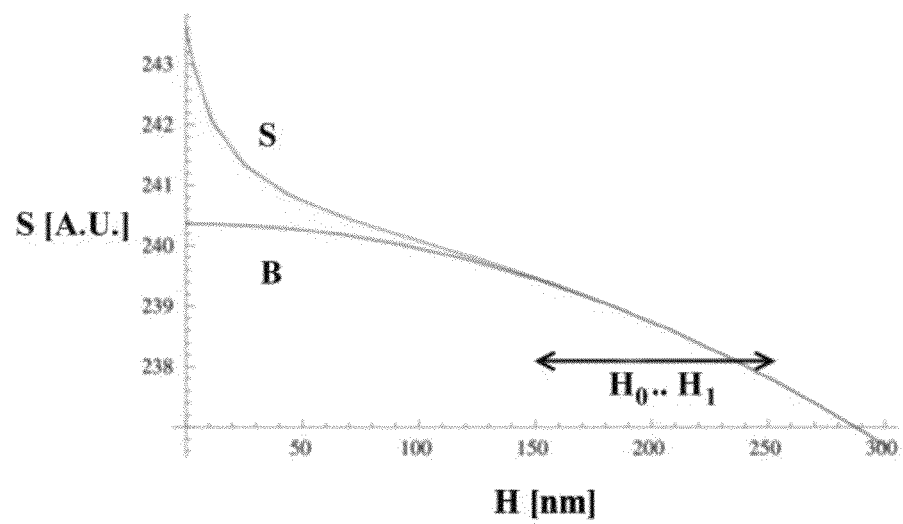
FIG. 4 shows two diagrams illustrating the scattering signal amplitude (signal) in arbitrary units (A.U.) relative to the probe-sample distance H in nanometer. Near-field signal N is obtained by subtracting calculated background B from the scattering signal S.
Figure 4:
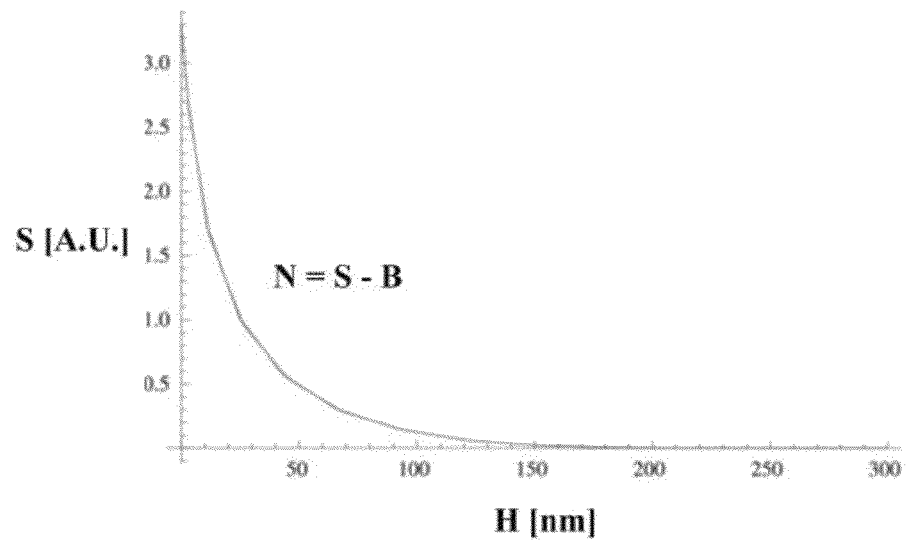

The upper diagram in FIG. 4 shows the scattering signal amplitude S relative to the probe-sample distance H. Curve S, i.e. the total scattering signal, is the sum of the near-field signal N and the background signal B. As shown in the upper diagram, in the range from 150 to 250 nanometers the total scattering signal substantially consists of background signal. Thus, the total scattering signal S can be used in the range $H_0$ to $H_1$ to determine fit coefficients for curve B based on the measured scattering signal S of the probe as a function of the distance H. The near-field signal N, which is a difference of total scattering signal S and the background signal B, can then be determined in the proximity of the sample, e.g. at a distance of 5 nanometers to 20 nanometers, by subtracting the background signal calculated according to the function for the background signal B determined from the scattering signal S (cf. diagram at the bottom of FIG. 4).

With the method according to the present invention, even the unmodulated part of the near-field signal N0, which is typically one order of magnitude higher than modulated near-field signal (cf. FIG. 1) can be detected.

The invention claimed is:

1. A method for measuring the near field signal of a sample in a scattering type near field microscope comprising a probe and a sample, wherein said method comprises the steps of:
   a) measuring the scattering signal S of the probe as a function of a distance-determining parameter P, whereby the functional dependence H(P) of the probe-sample distance H on P is known, by measuring the scattering signal S(P) for at least two values of the distance-determining parameter P corresponding to two probe-sample distances H in the range $H_0$ to $H_1$, wherein $H_1$ is larger than $H_0$, and the scattering signal S substantially consists of background signal for all distances $H > H_0$,
   b) determining the fit coefficients of a background fit function B(P), wherein the background fit function is equation (I):

$$B(P)=c0+c1*(\exp(i*k*H(P))+c2*\exp(-i*k*H(P)))^2 \quad (I),$$

wherein B(P) is the scattering signal S(P) as measured in step a), c0, c1 and c2 are fit coefficients, k is a fixed parameter or a fit coefficient, or wherein the background fit function B(P) is an at least first order approximation of equation (I) in terms of P,
   c) measuring the scattering signal $S_N$ of the probe for at least one value of the distance-determining parameter $P_N$ corresponding to a probe-sample distance $H_N$ smaller than $H_0$, and
   d) determining the near field signal N for at least one value of the distance-determining parameter $P_N$ by subtracting from the scattering signal $S_N$ measured at step c) the background signal $B_N$ which is calculated by extrapolating the background fit function B(P) to the probe-sample distance $H_N$ using the fit coefficients determined in step b).

2. The method according to claim 1, wherein the background fit function B(P) is equation (II):

$$B(P)=c0+(c1*H(P)) \quad (II),$$

wherein B(P) is the scattering signal S(P) as measured in step a), and c0 and c1 are fit coefficients.

3. The method according to claim 1, wherein the background fit function B(P) is equation (III):

$$B(P)=c0+(c1*H(P))+(c2*(H(P))^2) \quad (III),$$

wherein B(P) is the scattering signal S(P) for as measured in step a), and c0, c1 and c2 are fit coefficients.

4. The method according to claim 1, wherein the background fit function B(P) is equation (I) and k is a fixed parameter according to the equation (IV):

$$k=2*\pi/\lambda*\cos(\theta) \quad (IV),$$

wherein λ is the wavelength of the light illuminating the probe, θ is the mean angle of light incidence onto the tip of the probe relative to the probe oscillation.

5. The method according to claim 1, wherein the value of the distance-determining parameter P corresponds to any of the following quantities: the probe-sample distance H, the voltage applied to an actuator regulating the probe-sample distance, the vertical position Z of the sample or the probe as obtainable from a Z-position sensor, or a value corresponding to time T if the probe-sample distance H predictably depends on time, e.g. in case of an oscillating probe.

6. The method according to claim 1, wherein the fit coefficients are complex.

7. The method according to claim 1, wherein the near field signal is determined for a distance $H_N$ lower than 20 nm.

8. The method according to claim 1, wherein the distance $H_0$ is at least 100 nm.

9. The method according to claim 1, wherein the distance $H_1$ is at least 20 nm.

10. The method according to claim 1, wherein a near-field scan of the near-field signal of the sample is determined by raster-scanning the probe over the sample or raster-scanning the sample below the probe, and determining the near-field signal N for several scan positions.

11. The method according to claim 10, wherein step a) is conducted for each scan position for which the near-field signal N is determined.

12. The method according to claim 10, wherein step a) is conducted at least once before, after or during one scan of the sample.

13. The method according to claim 1, wherein the probe is oscillating substantially perpendicular to the sample and step a) is conducted during at least one oscillation cycle or an average oscillation cycle corresponding to a sum or a mean value of a number of oscillation cycles.

14. The method according to claim 1, wherein the near field signal is determined for a distance $H_N$ lower than 5 nm.

15. The method according to claim 1, wherein the distance $H_0$ is at least 150 nm.

16. The method according to claim 1, wherein the distance $H_1$ is at least 50 nm larger than $H_0$.

17. A device for measuring the near field signal of a sample, wherein said device is configured to conduct the method according to claim 1.

18. The device according to the claim 17, wherein the scattering signal is measured by an interferometric detection method.

* * * * *